United States Patent [19]
Grady

[11] Patent Number: 5,724,402
[45] Date of Patent: Mar. 3, 1998

[54] X-RAY SYSTEM WITH IMAGE DIRECTING OPTICS

[76] Inventor: John K. Grady, XRE Corporation 300 Foster St., Littleton, Mass. 01460

[21] Appl. No.: 611,885

[22] Filed: Mar. 6, 1996

[51] Int. Cl.$^6$ .................................................. H04N 1/00
[52] U.S. Cl. ............................... 378/98.3; 378/98.2
[58] Field of Search ........................ 378/98.2, 98.3, 378/98, 62

[56] References Cited

U.S. PATENT DOCUMENTS

| | | | |
|---|---|---|---|
| 3,038,959 | 6/1962 | Beurle | 378/98.3 |
| 4,593,400 | 6/1986 | Mouyen | 378/98.3 X |
| 5,008,547 | 4/1991 | Molteni et al. | 378/98.3 X |
| 5,023,896 | 6/1991 | Yokouchi et al. | 378/98.3 |
| 5,404,387 | 4/1995 | Hammond et al. | 378/98.3 |
| 5,412,705 | 5/1995 | Snoeren et al. | 378/98.3 |

*Primary Examiner*—David P. Porta
*Attorney, Agent, or Firm*—James H. Grover

[57] ABSTRACT

An X-ray system includes an X-ray source transmitting x-radiation through an radio-opaque mask and the position of a human subject to an X-ray receptor such as a fluorescent screen which responds to the X-radiation to produce a light image at the second side of the receptor. Effective at the second side of the receptor are a plurality of optical reflecting or refracting components in a two-dimensional pixel array which direct light from the image to the input lens of a video camera tube. That is, the optical components are spaced center-to-center proportionally to the size and spacing of the picture elements in a video signal generated by the camera tube. Because the light image is directed by the optical components selectively toward the input to the camera tube a substantially higher light energy is received by the camera tube than if the light from the receptor is radiated isotropically, such that the exposure of the subject is reduced and the signal-to-noise ration is increased, and the information content of the video signal is substantially improved.

31 Claims, 5 Drawing Sheets

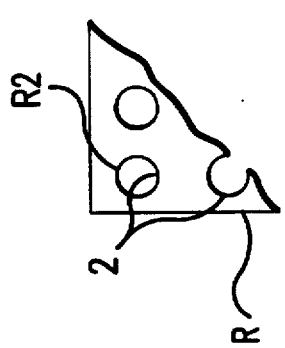
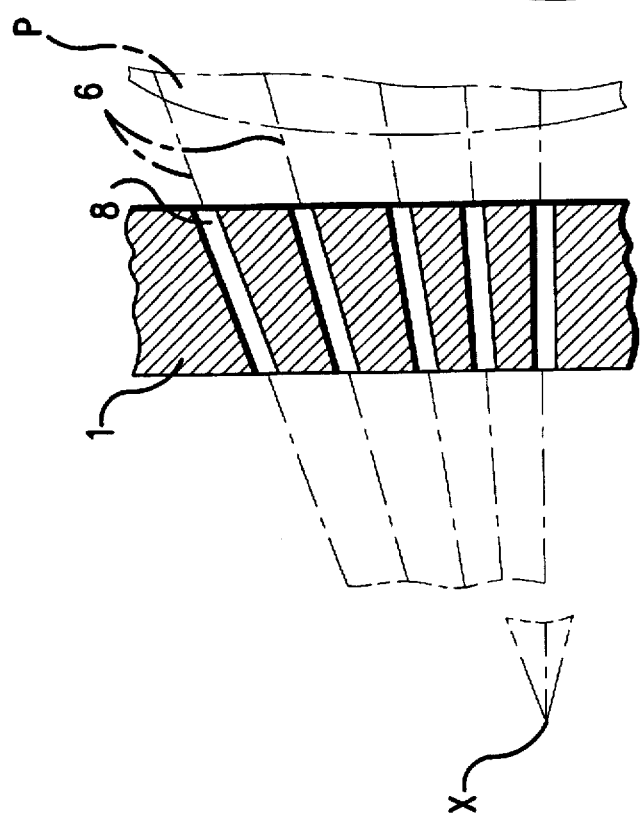
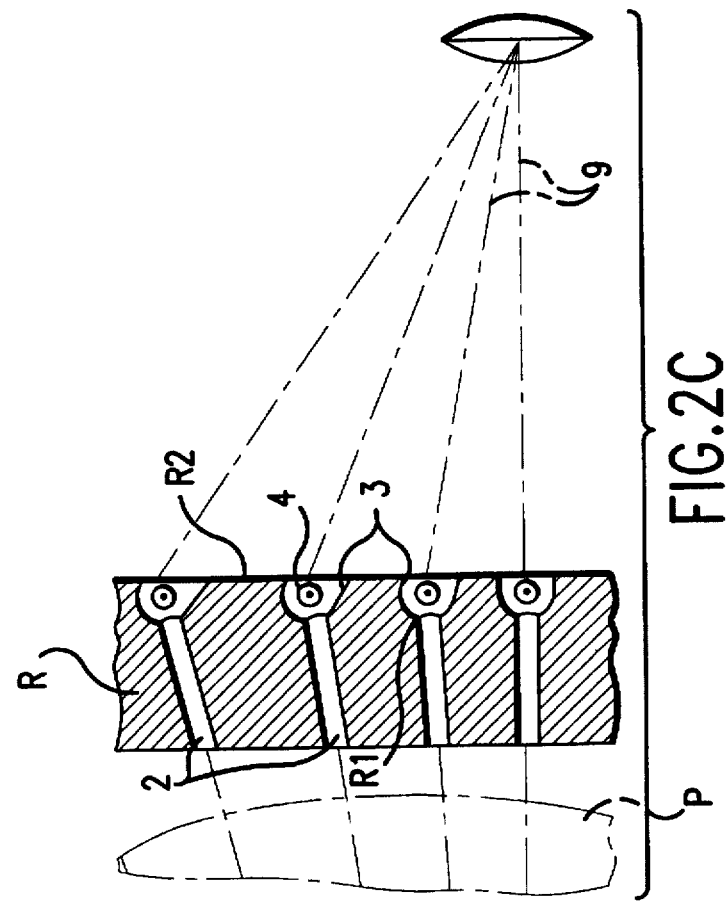

X-RAY SYSTEM WITH IMAGE DIRECTING OPTICS

BACKGROUND OF THE INVENTION

A longstanding radiological problem results from the inefficient use of light produced when X-rays, after passing through a subject such as a human patient, strike an X-ray receptor such as a fluorescent screen and are converted into a light image corresponding to the subject. Photons from the light image are typically sensed by a video camera tube or like utilization means which views the light image with an input lens necessarily spaced from the light image. Because light is emitted from a point source in an essentially spherical manner, light intensity decreases as a function of the distance of the utilization input lens from the fluorescent image, and less than 1% of photons emitted by the receptor are captured by the lens for utilization in generating an electronic signal for printing or displaying the light image on a cathode ray screen. Signal fidelity is lost by a decrease in the signal to noise ratio, and harmful X-ray dosage must be increased to compensate for the loss.

It is the object of the present invention to provide an X-ray system which more efficiently directs light from a fluorescent light image to the input of a video camera or like light image utilization means so as to increase the signal-to-noise ratio, strength and resolution of the resulting video signal while reducing the X-ray exposure of the patient.

SUMMARY OF THE INVENTION

According to the invention an improved X-ray system for radiological examination of a subject comprises an X-ray source directing radiation through a subject position, an X-ray receptor beyond the subject position with a first side in the X-ray beam path facing the subject position and a second side, the receptor including X-radiation responsive means forming at the second side a light image of the subject, means for utilization of the light image and a plurality of optical components at the opposite side of the X-ray receptor for directing the light image to the utilization means.

There may be multiple utilization means multiple cameras and camera arrays) commensurate with the number of light directing optics.

DRAWINGS

FIG. 2 is an enlarged view of a portion of the X-ray receptor in the system of FIG. 1;

FIG. 2A is a fragmentary front view of the receptor of FIG. 1;

Figure 1:
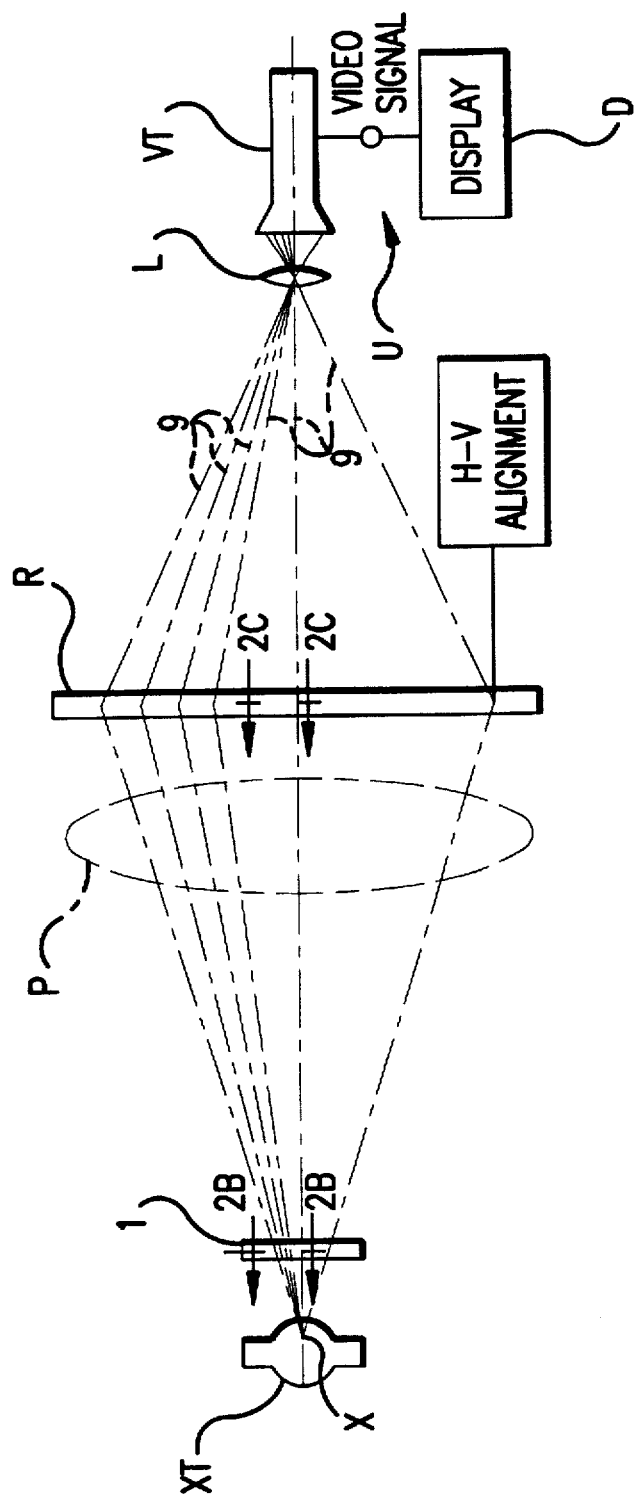
FIG. 1 is a schematic optical drawing of one form of an X-ray system with a light directing X-ray receptor according to the invention.
Figure 3:
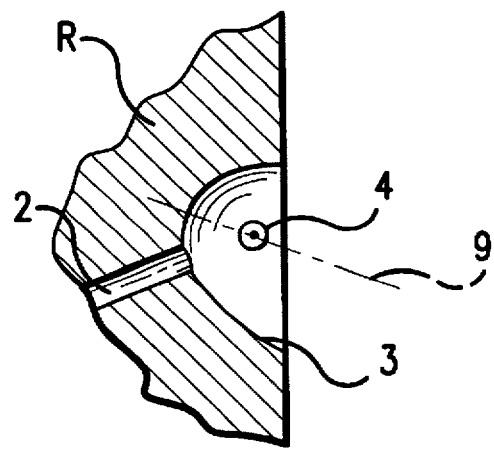
Figure 4:
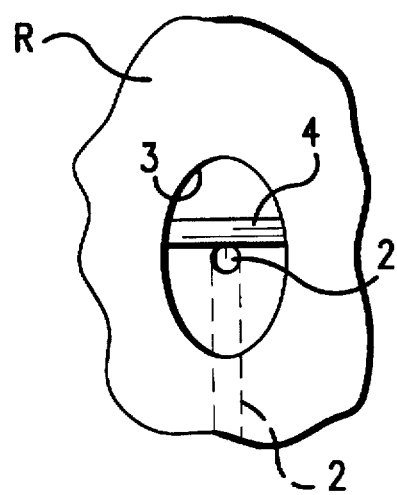
Figure 5:
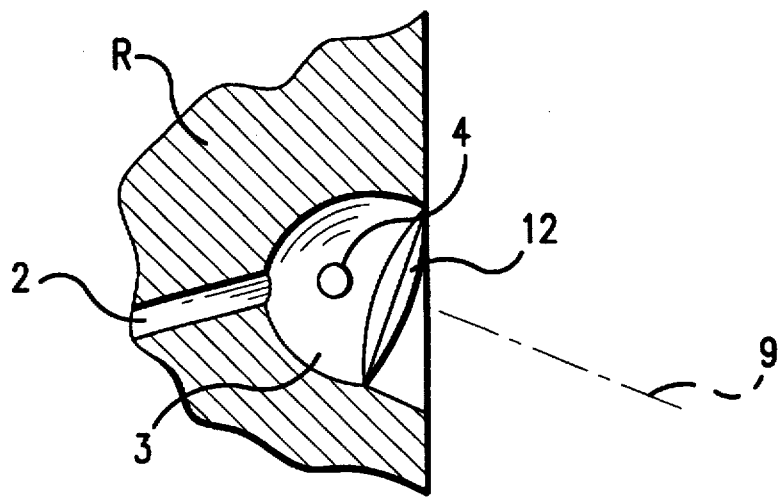
Figure 6:
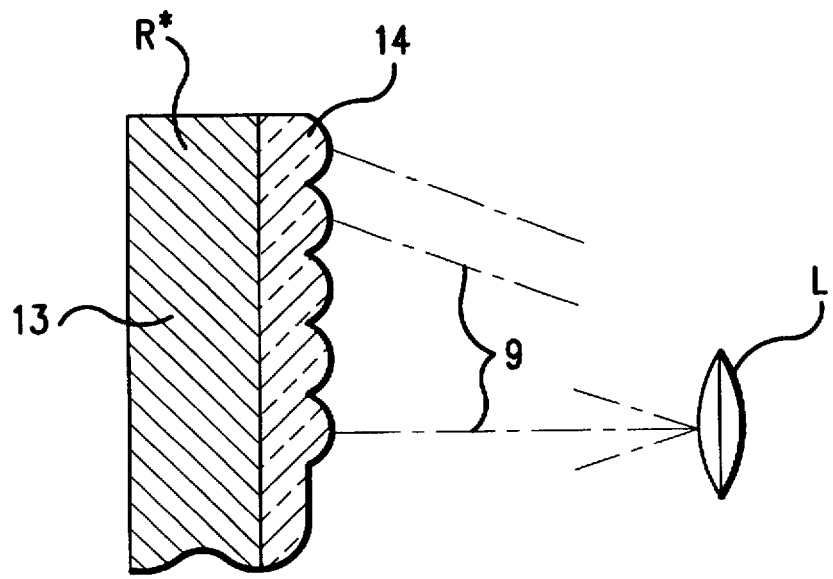
Figure 7:
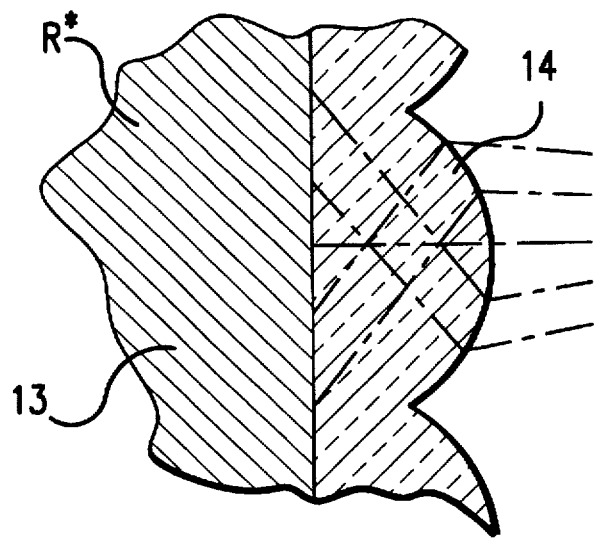
Figure 8:
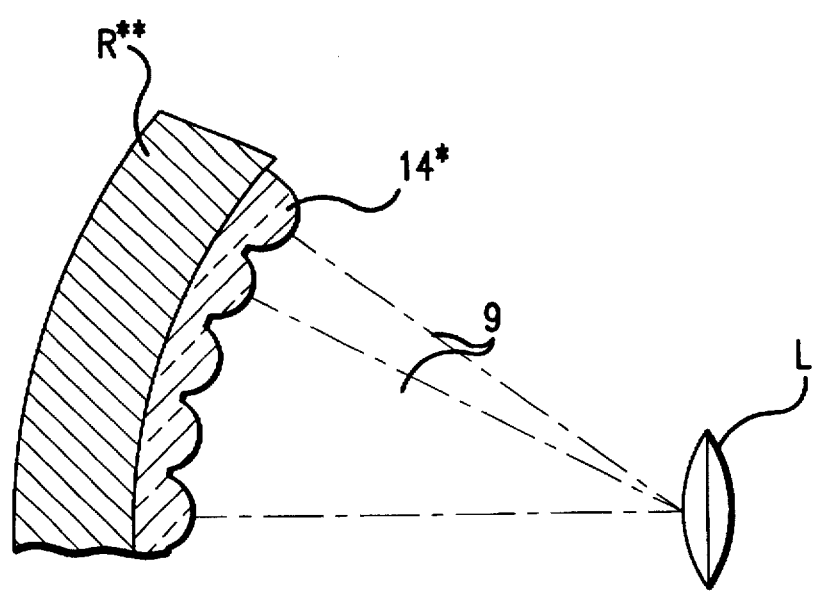

FIG. 3. is a further enlarged sectional view of a detail of the X-ray receptor in FIG. 2;

FIG. 4 is a front elevation of the detail of FIG. 3;

FIG. 5 is a enlarged sectional view showing a modification of the detail of FIG. 3;

FIG. 6 is an enlarged sectional view of another form of X-ray receptor detail;

FIG. 7 is a still further enlarged sectional view of the X-ray receptor detail of FIG. 6; and FIG. 8 is an enlarged sectional view of a further form of X-ray receptor detail.

DESCRIPTION

One form of the invention is shown in FIGS. 1 to 5 in which an X-ray tube XT emits X-radiation from a focal spot X through a radio-opaque mask 1 and the position P of a subject, such as a human patient, to an X-ray receptor R. The X-ray receptor comprises a screen of fluorescent material which forms a light image of the subject in the position P. This light image is viewed by the input lens L of means such as a video camera tube VT utilizing the light image to generate video signals for display on a cathode ray monitor D or for graphic printout.

As shown in FIGS. 2 and 2A, the X-ray receptor R has a two-dimensional array of passages 2 from its first side R1 beyond the subject position, through the receptor, to its second side R2. The passages terminate in minute spaces 3 at the second side of the receptor, the spaces being disposed in the same two-dimensional array as the passages. Within the spaces 3 are small units 4 of X-radiation responsive, e.g. fluorescent or phosphorescent, material which emit light corresponding to the X-rays transmitted from the subject position.

Before reaching the subject position P the X-radiation from the tube XT is collimated into discrete beams 6 by a mask 1 of X-ray opaque metal such as lead. The mask 1 has an array of X-ray transmissive windows 8 through it which form discrete beams diverging toward the receptor R. The windows 8 are in a two-dimensional array optically corresponding to area of the subject position and consequently to the two dimensional array of passages 2, terminal spaces 3 and light emitting units 4 in the receptor R. This two-dimensional array has a size and spacing proportional to the picture element, i.e. pixel spacing, of the image in the display D of FIG. 1. A typical pixel spacing in an medical X-ray print or display is 100 to 1000 microns. The greater spacing of the windows in the mask and the passages and of the light emitting units in the receptor is simply calculated from the sizes of the mask and receptor relative to the size of the display.

The angular divergence of collimated rays 6 passed by the mask 7 is adjusted so that each discrete ray travels through a corresponding passage 2 of the receptor to a radiation responsive unit 4 in a space 3 at its second side. Preferably the light emitted by an individual unit is redirected toward the input lens L of the utilization means by an optical component in the space. As shown in FIGS. 3 and 4 the space 3 itself may comprise an ellipsoidal, parabolic or like concave coated reflector with the light emitting unit 4 at its focus so as to concentrate the light on paths 9 to the lens L. Alternatively, as shown in FIG. 5 the optical component may be a refractor such as a lens 12.

An alternative form of receptor R* shown in FIGS. 6 to 8 comprises a homogeneous body 13 of fluorescent material with integral lenticular refractors 14 embossed by known processes on the second side of the receptor. The lenticules in FIG. 6 are formed on a planar receptor with a refracting shape redirecting light from the receptor on converging rays 9 to the input lens L of the utilization means. In FIG. 8 the receptor body R** is of concave shape with lenticules 14* directing light to the lens by virtue of the receptor body curvature.

By redirecting rays from the light image selectively toward the input optics of the utilization means the X-radiation receptors of FIGS. 1 to 5, of FIGS. 6 and 7 and of FIG. 8 greatly reduce the light and definition loss inherent in prior receptors wherein light of the image viewed is propagated in all directions with only a small percentage, as little as 1%, reaching the input optics of the video signal generator.

I claim:

1. An X-ray system for radiological examination of a subject comprising:

an X-ray source directing radiation through a subject position;

a planar X-ray receptor beyond the subject position with a first side in the X-ray beam path facing the subject position and an opposite side, the receptor including a plurality of X-radiation responsive units forming at the opposite side a light image of the subject at the opposite side;

means for utilization of the light image and a plurality of optical components at the opposite side of the X-ray receptor respectively adjacent the radiation responsive units for directing light from respective units in different rays through space at different angles to the utilization means.

2. A system according to claim 1 wherein the optical components are reflectors.

3. A system according to claim 1 wherein the optical components are refractors.

4. A system according to claim 1 wherein the X-radiation responsive means are disposed in a two-dimensional pixel array corresponding to the subject.

5. A system according to claim 1 wherein the optical components are disposed in a two-dimensional pixel array corresponding to the radiation responsive units.

6. A system according to claim 5 including an X-ray-opaque mask between the X-ray source and the X-ray receptor, the mask having an array of X-ray windows therethrough passing a pattern of X-ray beams matching the pixel array of optical components on the second side of the receptor.

7. A system according to claim 1 wherein the utilization means is a video camera tube converting the light image to a video signal.

8. A system according to claim 1 wherein the X-radiation responsive units and the optical components are disposed in a two-dimensional pixel array corresponding to the subject.

9. A system according to claim 1 wherein each optical component is disposed in a position relative to one of the X-radiation responsive units to redirect light from the X-radiation means at a selected angle toward the utilization means.

10. A system according to claim 1 wherein the X-radiation responsive units are pixel-sized units of fluorescent material.

11. A system according to claim 1 wherein the X-ray receptor has a two-dimensional array of X-ray transmissive passages from the first through to the second side.

12. A system according to claim 11 including an X-ray-opaque mask between the X-ray source and the X-ray receptor, the mask having an array of X-ray windows therethrough passing a pattern of X-ray beams matching the two-dimensional array of passages through the receptor.

13. A system according to claim 11 wherein the passages terminate in a two-dimensional array of spaces at the second side of the receptor.

14. A system according to claim 13 wherein each space contains a pixel-sized unit of X-radiation responsive material emitting light corresponding to the subject.

15. A system according to claim 12 wherein each space includes an optical component directing light from the pixel-sized unit toward the utilization means.

16. A system according to claim 1 wherein the planar X-ray receptor comprises a body of X-ray responsive material displaying at its second side a light image of the subject.

17. A system according to claim 16 wherein the body has at its second side a two-dimensional array of pixel-sized lenticules redirecting light from the second side of the receptor to the utilization means.

18. A system according to claim 17 wherein the lenticules direct light beams converging toward the utilization means.

19. A system according to claim 1 wherein the X-ray receptor is planar.

20. A system according to claim 1 wherein the X-ray receptor is concave at its second side.

21. A system according to claim 16 wherein the X-ray receptor is concave at its second side.

22. An X-ray system for radiological examination of a subject comprising:

an X-ray source directing radiation through a subject position;

a X-ray receptor beyond the subject position with a body having a first side in the X-ray beam path facing the subject position and a second side, the receptor including X-radiation responsive means forming at the second side a light image of the subject;

means for utilization of the light image and a plurality of pixel sized lenticules at the opposite side of the X-ray receptor for directing the light image to the utilization means.

23. A system according to claim 22 wherein the X-ray receptor is planar.

24. A system according to claim 22 wherein the X-ray receptor is concave at its second side holding the axes of the lenticules directed at different angles toward the utilization means.

25. An X-ray receptor for responding to X-rays received through a subject under examination comprising:

a body having a first side receiving X-rays and a second side, the body having a plurality of pixel-sized X-radiation responsive units forming a light image at the second side; and a plurality of optical component at the second side for directing light away from the second side at different angles through space toward a common focal plane.

26. An X-ray receptor according to claim 25 wherein the optical components are refractors.

27. An X-ray receptor according to claim 25 wherein the optical components are lenticules.

28. An X-ray receptor according to claim 25 wherein the second side of the X-ray receptor is concave.

29. An X-ray receptor according to claim 1 wherein the optical components are reflectors with optical axes.

30. An X-ray receptor according to claim 1 wherein the X-radiation means comprises pixel-sized units of fluorescent material on the optical axes of respective reflectors.

31. An X-ray receptor according to claim 1 wherein the receptor body has a two-dimensional array of passages between its first and second sides, the passages terminating in spaces forming reflectors redirecting light from respective units of fluorescent material.

\* \* \* \* \*